(12) United States Patent
Ohta et al.

(10) Patent No.: US 8,222,612 B2
(45) Date of Patent: Jul. 17, 2012

(54) RADIATION IMAGE CAPTURING APPARATUS

(75) Inventors: Yasunori Ohta, Yokohama (JP); Kazuo Hakamata, Odawara (JP); Kuniaki Miyako, Minami-ashigara (JP); Hajime Nakata, Minami-ashigara (JP); Yuto Tanaka, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

(21) Appl. No.: 12/239,670

(22) Filed: Sep. 26, 2008

(65) Prior Publication Data

US 2009/0084971 A1 Apr. 2, 2009

(30) Foreign Application Priority Data

Sep. 28, 2007 (JP) ................................. 2007-253777

(51) Int. Cl.
*G01T 1/24* (2006.01)
(52) U.S. Cl. ................................................. 250/370.15
(58) Field of Classification Search .............. 250/370.15
See application file for complete search history.

(56) References Cited

U.S. PATENT DOCUMENTS

| | | | |
|---|---|---|---|
| 6,323,891 B1 | 11/2001 | Kitani et al. | |
| 6,483,567 B1 | 11/2002 | Okada | |
| 6,667,480 B2 | 12/2003 | Kajiwara et al. | |
| 6,812,494 B2 | 11/2004 | Mochizuki et al. | |
| 7,450,174 B2 | 11/2008 | Watanabe et al. | |
| 2002/0011572 A1 * | 1/2002 | Kajiwara et al. | 250/370.11 |
| 2003/0066672 A1 * | 4/2003 | Watchko et al. | 174/50 |
| 2003/0085359 A1 * | 5/2003 | Dailey et al. | 250/370.15 |
| 2004/0256567 A1 * | 12/2004 | Nokita | 250/370.08 |
| 2005/0087694 A1 * | 4/2005 | Shoji | 250/370.09 |
| 2007/0221859 A1 * | 9/2007 | Nakata | 250/370.15 |
| 2007/0267577 A1 * | 11/2007 | Kindem | 250/370.15 |

FOREIGN PATENT DOCUMENTS

| | | |
|---|---|---|
| EP | 943931 A2 * | 9/1999 |
| JP | 06-021290 A | 1/1994 |
| JP | 07-140255 A | 6/1995 |
| JP | 10-177224 A | 6/1998 |
| JP | 11-026968 A | 1/1999 |
| JP | 11-345956 A | 12/1999 |
| JP | 2000-105297 A | 4/2000 |
| JP | 2000-112369 A | 4/2000 |
| JP | 2000-124652 A | 4/2000 |
| JP | 2000-131500 A | 5/2000 |
| JP | 2000-258541 A | 9/2000 |
| JP | 2001-099942 A | 4/2001 |
| JP | 2001-198116 A | 7/2001 |

(Continued)

OTHER PUBLICATIONS

Rejection of the Application, dated Jul. 27, 2010, issued in corresponding JP Application No. 2007-253777, 4 pages in English and Japanese.

*Primary Examiner* — David Porta
*Assistant Examiner* — Shun Lee
(74) *Attorney, Agent, or Firm* — Sughrue Mion, PLLC (57) ABSTRACT

The present invention relates to a radiation image capturing apparatus, and includes a radiation image information detector for detecting radiation image information of a subject, a casing containing the radiation image information detector, a reading circuit for reading the radiation image information from the radiation image information detector, and a heat release unit for fastening the reading circuit and releasing heat generated by the reading circuit to the casing.

53 Claims, 9 Drawing Sheets

FOREIGN PATENT DOCUMENTS

| | | |
|---|---|---|
| JP | 2002-022841 A | 1/2002 |
| JP | 2002-050754 A | 2/2002 |
| JP | 2002-116261 A | 4/2002 |
| JP | 2002-182795 A | 6/2002 |
| JP | 2002-250773 A | 9/2002 |
| JP | 2003-194951 A | 7/2003 |
| JP | 2003-218570 A | 7/2003 |
| JP | 2004-177250 A | 6/2004 |
| JP | 2005-283262 A | 10/2005 |
| JP | 2007-215929 A | 8/2007 |

* cited by examiner

PRIOR ART

RADIATION IMAGE CAPTURING APPARATUS

BACKGROUND OF THE INVENTION

1. Field of the Invention

The present invention relates to a radiation image capturing apparatus for capturing a radiation image of a subject using a radiation image information detector.

2. Description of the Related Art

In the medical field, for example, radiation image capturing apparatuses are extensively used, which acquire radiation image information by irradiating a subject (patient) with radiation emitted from a radiation source, and detecting the radiation that has passed through the subject with a radiation image information detector.

In a radiation image capturing apparatus provided with a radiation image information detector, an image signal (radiation image information) produced by the radiation image information detector is read out from the detector, amplified by an amplifier, and transmitted to an image processing apparatus that performs image processing on the image signal. Since the radiation image information detector generates the image signal from a very small amount of charge, the image signal tends to be affected by even small temperature variations in the radiation image information detector, the amplifier, and the like.

Figure 9:
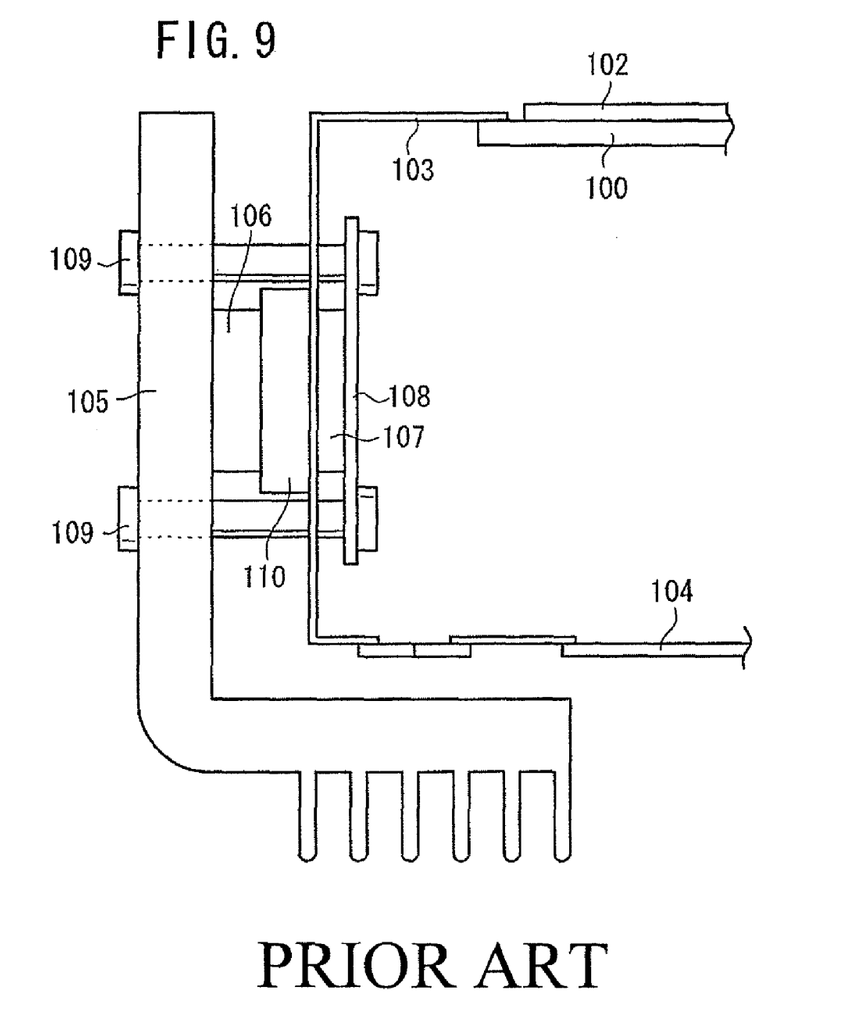
FIG. 9 is a schematic side view of a conventional radiation image capturing apparatus.

Japanese Laid-Open Patent Publication No. 2002-022841 discloses a radiation image capturing apparatus capable of producing an image signal that is particularly stable with respect to temperature variation of the amplifier. This radiation image capturing apparatus includes, as shown in FIG. 9, a glass sensor substrate 100 on which a plurality of pixels are formed. Each pixel is a conversion unit that includes a photoelectric conversion element and a thin film transistor (TFT). A phosphor layer 102 is further formed on the sensor substrate 100.

A flexible substrate 103, which serves as signal lines, is connected to the sensor substrate 100 and also to a signal processing circuit board 104, and a detection integrated circuit 110, which is an amplifying means, is mounted on the flexible substrate 103. A cooling fin 105 is attached to the integrated circuit (IC) 110, with a heat transmitting member 106 disposed between the IC 110 and the cooling fin 105, in order to release heat generated by the integrated circuit 110. The cooling fin 105 is supported by sleeves 109 that are attached to the flexible substrate 103 by an elastic member 107 and a fastening plate 108 arranged on the opposite side of the flexible substrate 103 to the integrated circuit 110.

However, the apparatus described in Japanese Laid-Open Patent Publication No. 2002-022841 requires a substantially large cooling fin 105 to achieve sufficient heat release, and thus raises a problem in that the size of the apparatus may have to be increased to contain the large cooling fin 105.

Especially in X-ray breast image capturing apparatuses (mammography apparatuses) that capture a radiation image of a breast of a subject by exposing the breast to radiation, it is difficult to increase the size of the image capturing base in which the radiation image information detector is housed, due to the configuration of the apparatus. Hence, the heat release technique described in the Japanese Laid-Open Patent Publication No. 2002-022841 is not easily applied to such apparatuses.

SUMMARY OF THE INVENTION

It is a general object of the invention to provide a radiation image capturing apparatus that is capable of suitably releasing heat of electronic components during their operation while achieving downsizing of the apparatus.

It is a main object of the invention to provide a radiation image capturing apparatus that is capable of fastening the electronic components and thereby effectively protecting the electronic components from vibration and the like while suitably releasing heat of the electronic components, which are heat generators.

It is another object of the invention to provide a radiation image capturing apparatus that is capable of releasing heat to outside with a simple configuration that needs no cooling means.

A radiation image capturing apparatus according to the present invention comprises a radiation image information detector for detecting radiation image information of a subject, a casing containing the radiation image information detector, a reading circuit for reading the radiation image information from the radiation image information detector, and a heat release unit for fastening the reading circuit and releasing heat generated by the reading circuit to the casing.

In the above-described arrangement, by providing the heat release unit, it is possible to fasten the reading circuit reliably and thereby to effectively protect the reading circuit and signal lines connecting the reading circuit and the detection unit of the radiation image information detector from vibration and the like. Further, the heat release unit is capable of suitably releasing heat of the reading circuit during its operation from a casing. That is, the casing containing the radiation image information detector can be utilized as a radiator of the reading circuit. Therefore, there is no need for additional fastening members, radiation fins or the like for the reading circuit in the casing. Thus, the apparatus can be made in a more simple and compact configuration.

In this configuration, the heat release unit may include a first heat release member and a second heat release member, the first heat release member being fastened to the casing, the second heat release member being fastened to the first heat release member with the reading circuit held between the first and second heat release members. Then, the reading circuit can be fastened more reliably, and its heat release efficiency can be increased.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Hereinafter, a preferred embodiment of a radiation image capturing apparatus according to the present invention will be described with reference to the drawings.

Figure 1:
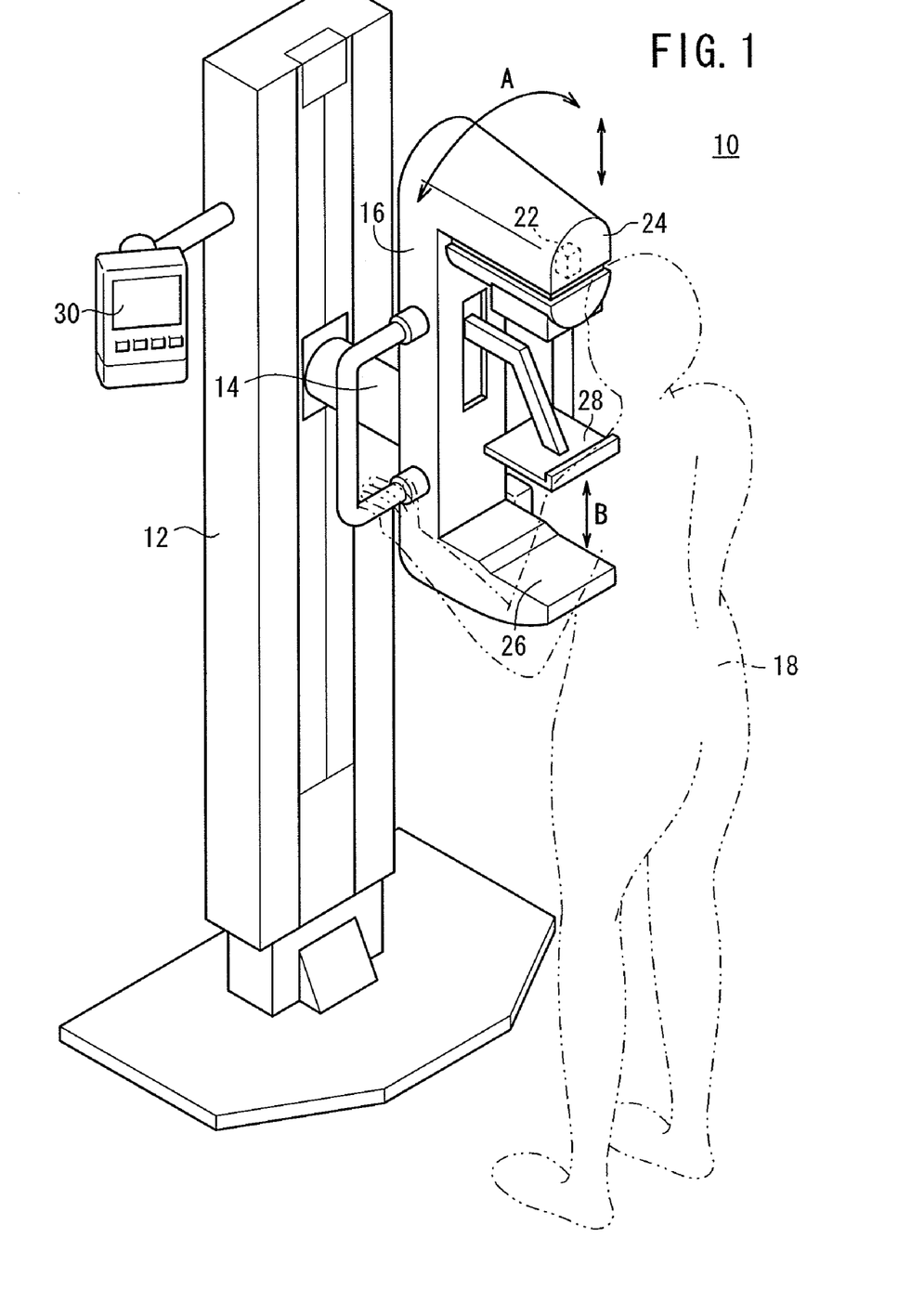
FIG. 1 is a perspective view illustrating a mammography apparatus as a radiation image capturing apparatus according to an embodiment of the present invention.

FIG. 1 is a perspective view of a mammography apparatus 10 as the radiation image capturing apparatus according to an embodiment of the present invention. It should be noted that although the mammography apparatus 10 will be described hereinafter as an embodiment of the radiation image capturing apparatus according to the present invention, the present invention is not limited to the mammography apparatus 10.

The mammography apparatus 10 includes an upstanding base 12, an arm 16 fixed to a pivot shaft 14 that is connected substantially centrally to the base 12, a radiation source housing unit 24 fixed to one end of the arm 16 and housing a radiation source 22 for applying radiation X to a breast 20 (see FIG. 2) which is the image capturing site of a subject 18, an image capturing base 26 fixed to the other end of the arm 16 so as to oppose the radiation source housing unit 24, and a compression plate 28 for holding the breast 20 by compressing it against the image capturing base 26.

The arm 16 holding the radiation source housing unit 24 and the image capturing base 26 can be rotated about the pivot shaft 14 in the directions indicated by double-headed arrow A to adjust the image capturing direction of the breast 20 of the subject 18. The compression plate 28 is connected to the arm 16 between the radiation source housing unit 24 and the image capturing base 26 so as to be movable in the directions shown by double-headed arrow B. The base 12 is also provided with a display control panel 30 for displaying image capturing information of the image obtained by the mammography apparatus 10, and the identification (ID) information or the like of the subject 18. The image capturing information includes the image capturing site, image capturing direction, and the like of the image of the subject 18. The display control panel 30 also allows settings of the above-mentioned information, if desired.

Figure 2:
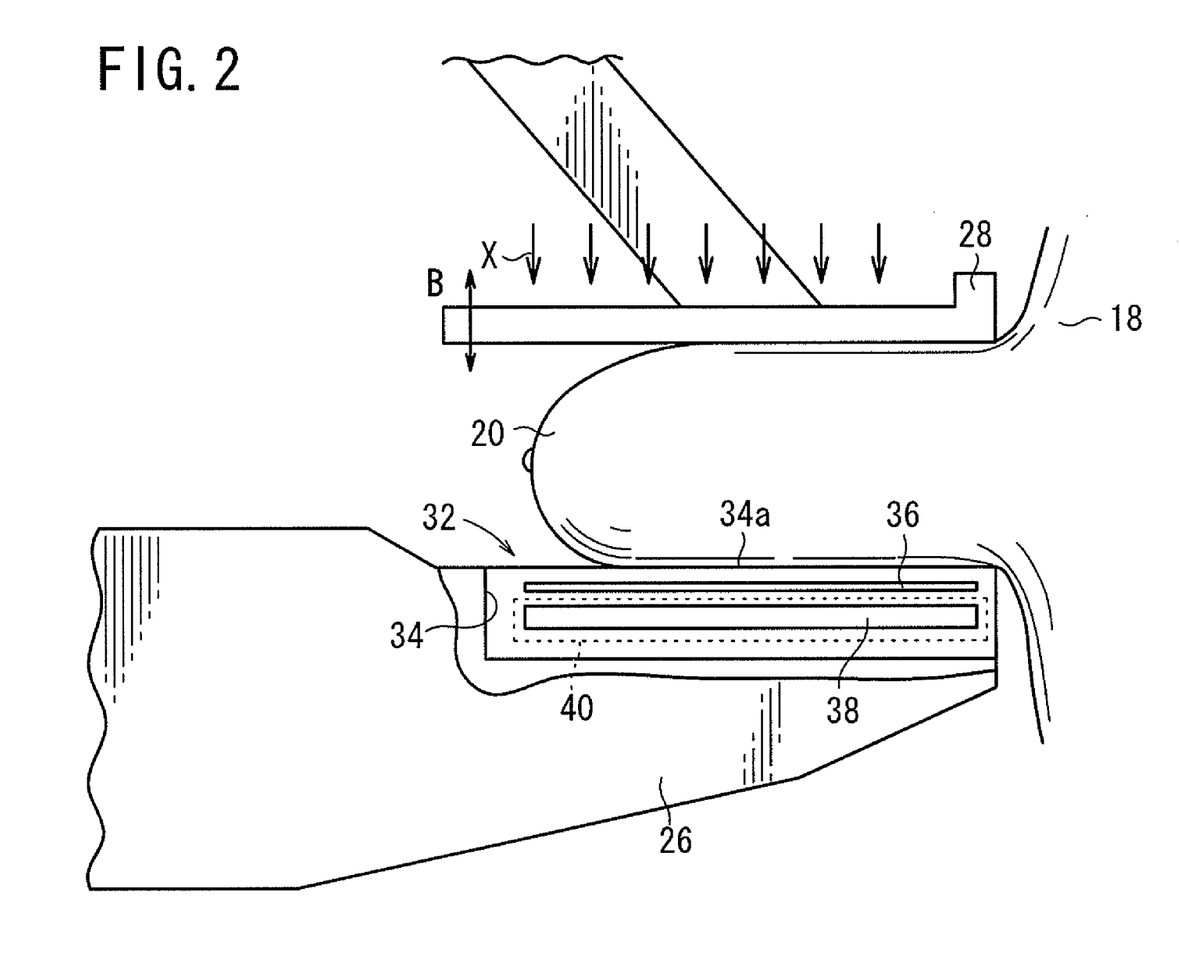
FIG. 2 is a diagram illustrating the internal structure of the image capturing base of the mammography apparatus shown in FIG. 1.

FIG. 2 is a diagram illustrating the internal structure of the image capturing base 26 of the mammography apparatus 10. In FIG. 2, the breast 20, i.e., the imaging capturing site of the subject 18, is placed between the image capturing base 26 and the compression plate 28.

A radiation detecting device 32 is disposed within the image capturing base 26. The radiation detecting device 32 includes a casing 34 which is the body of the radiation detecting device 32. The casing 34 has an irradiated surface 34a facing the radiation source 22 (the top surface of the radiation detecting device 32 in FIG. 2). In the casing 34, at least the irradiated surface 34a is made of a radiation transmissive material, and other sides of the casing 34 are made of a highly heat-conductive material. Disposed within the casing 34 are, in order from the irradiated surface 34a onto which radiation X is applied, a grid 36 for removing radiation X scattered by the subject 18, a solid-state radiation detector (radiation image information detector) 38 for detecting radiation X that has passed through the subject 18, a heat release member (heat release unit) 40 which fastens reading ICs 42 and signal lines 56 of the solid-state radiation detector 38 (see FIG. 3) and promotes the release of heat generated by the reading ICs 42. Note that the irradiated surface 34a of the casing 34 may also be configured so as to serve as the grid 36.

Figure 3:
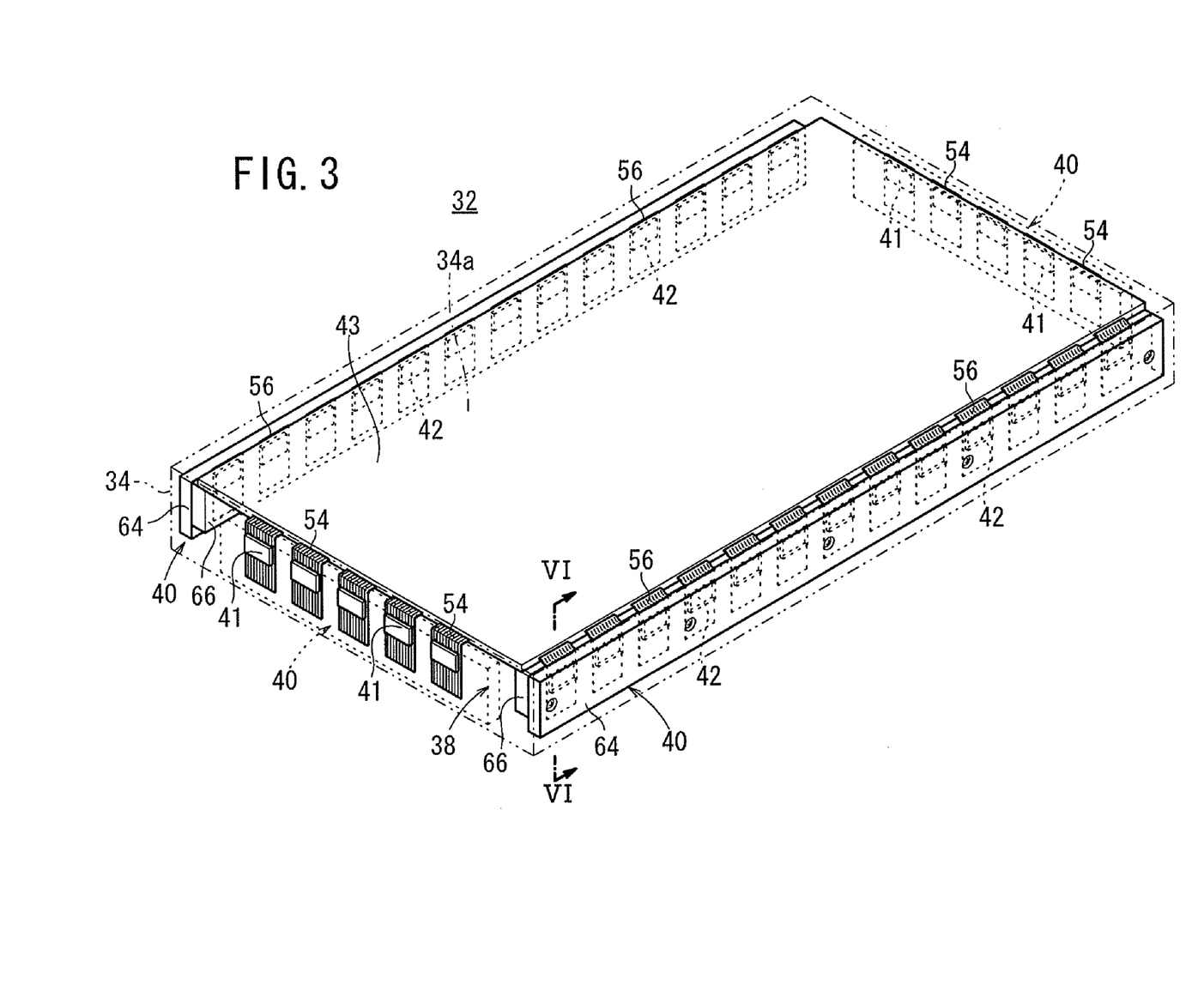
FIG. 3 is a partially-omitted schematic perspective view of a radiation detecting device that is arranged within the image capturing base shown in FIG. 1.

FIG. 3 is a partially-omitted schematic perspective view of the radiation detecting device 32 disposed within the image capturing base 26. It should be noted that the grid 36 is omitted from FIGS. 3 and 5.

The solid-state radiation detector 38 is a flat panel type radiation detector (FPD). The solid-state radiation detector 38 includes a sensor substrate (detection unit) 43 for storing radiation image information associated with the radiation X that has passed through the subject 18 in the form of two-dimensional charge information, a plurality of driving ICs 41 of a gate line driving circuit that drives gate lines 54 connected to the pixels of the sensor substrate 43, and a plurality of reading ICs (reading circuits) 42, which are application specified integrated circuits (ASICs), that make up a signal reading circuit for reading out the charge information via the signal lines 56 from pixels connected to the gate lines 54 in driven state. As shown in FIG. 3, the driving ICs 41 are attached to one pair of opposing sides of the sensor substrate 43, while the reading ICs 42 are attached to the other pair of opposing sides of the sensor substrate 43. The arrangement of the driving and reading ICs 41 and 42 on the sensor substrate 43, however, is not limited to that illustrated in FIG. 3, and the driving and reading ICs 41 and 42 may, for instance, be located together on the same single side of the sensor substrate 43.

Each of the reading ICs 42 is supplied with electrical current from the signal line 56 via a variable resistor device (not shown). The reading IC 42 includes an operational amplifier (not shown), an integrating capacitor (not shown), and the like for detecting the electrical current and serves as a reading circuit (amplifier) that reads out and amplifies the radiation image information from the sensor substrate 43, which is a radiation image information detector. The reading IC 42 generates a considerable amount of heat during operation. Hence, the reading ICs 42 are provided with the heat release member 40 described above. It should be understood that, as with the reading ICs 42 and the signal lines 56, the driving ICs 41 and the gate lines 54 may be provided with the heat release member 40 in order to fasten the driving ICs 41 and the gate lines 54 and release heat of the driving ICs 41 as indicated by broken line in FIG. 3. Note that, in the present embodiment, the signal lines 56 and the gate lines 54 connecting the reading ICs 42 and the driving ICs 41 to the sensor substrate 43, respectively, are flexible substrates, and the reading ICs 42 and the driving ICs 41 are mounted on these flexible substrates (see FIG. 5).

Figure 4:
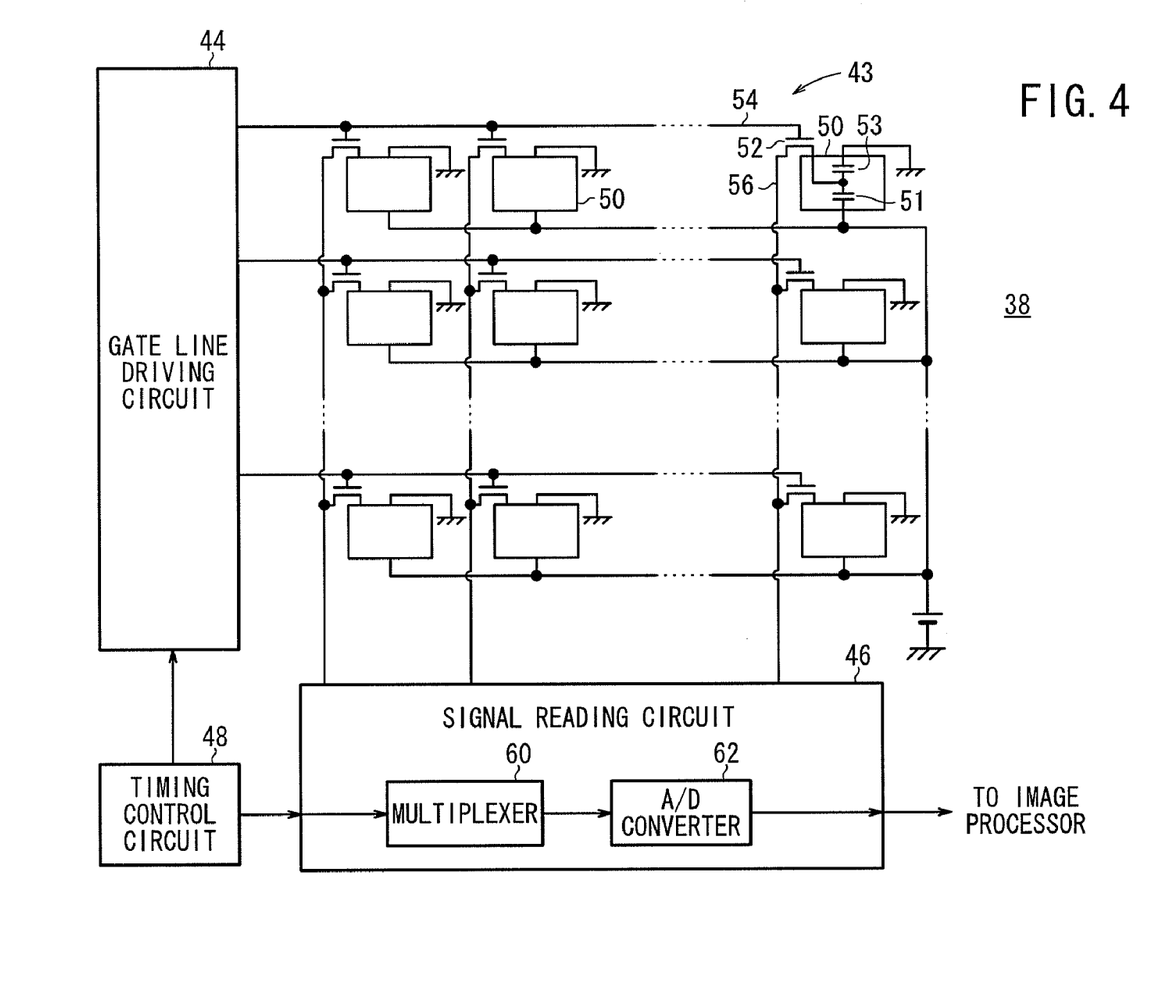
FIG. 4 is a block diagram illustrating the circuit configuration of the solid-state radiation detector shown in FIG. 2.

FIG. 4 is a block diagram showing a circuit configuration of the solid-state radiation detector 38. The solid-state radiation detector 38 includes the sensor substrate 43, a gate line driving circuit 44 made up of the plurality of driving ICs 41, a signal reading circuit (readout circuit) 46 made up of the plurality of reading ICs 42, and a timing control circuit 48 for controlling the gate line driving circuit 44 and the signal reading circuit 46.

The sensor substrate 43 includes a photoelectric conversion layer 51 placed over a two-dimensional array of thin film transistors (TFTs) 52. The photoelectric conversion layer 51 is made of a material such as amorphous selenium (a-Se), which generates electrical charge upon sensing radiation X. The generated charge is stored into a storage capacitor 53. Then, the TFTs 52 in each row of the two-dimensional array are sequentially switched on to allow the charges in the storage capacitors 53 to be read out as image signals. FIG. 4 only illustrates the connection between one TFT 52 and one pixel 50 made up of one storage capacitor 53 and the photoelectric conversion layer 51. The details of other pixels 50 are omitted for clarity. The TFT 52 of each pixel 50 is connected to one gate line 54 and one signal line 56 that extend, respectively, in the row direction and column direction of the TFT array. Each gate line 54 is connected to the gate line driving circuit 44, and each signal line 56 is connected to the signal reading circuit 46.

The signal reading circuit 46 includes a multiplexer 60 and an analog-to-digital (A/D) converter 62. The multiplexer 60 selects the pixels 50 connected to one of the signal lines 56 based on the timing control signal supplied from the timing control circuit 48. The A/D converter 62 coverts the radiation image information read out from the selected pixels 50 into a digital image signal and sends the digital image signal to an image processor 61 (see FIG. 7) which will be described later.

The solid-state radiation detector 38 generally shows performance degradation at high temperatures. One reason for this degradation is a structural change which occurs at high temperatures, e.g., in the amorphous selenium. To avoid this degradation, the solid-state radiation detector 38 must be used within a predetermined temperature range. The reading IC 42 serving as an amplifier, for example, generates a large amount of heat during operation. To produce a radiation image of the required high accuracy, the heat generated by the reading IC 42 should be released from the radiation detecting device 32. Hence, the radiation detecting device 32 of the mammography apparatus 10 according to the present embodiment is provided with the heat release member 40 that releases the heat generated by the reading IC 42 to outside via the casing 34.

Figure 5:
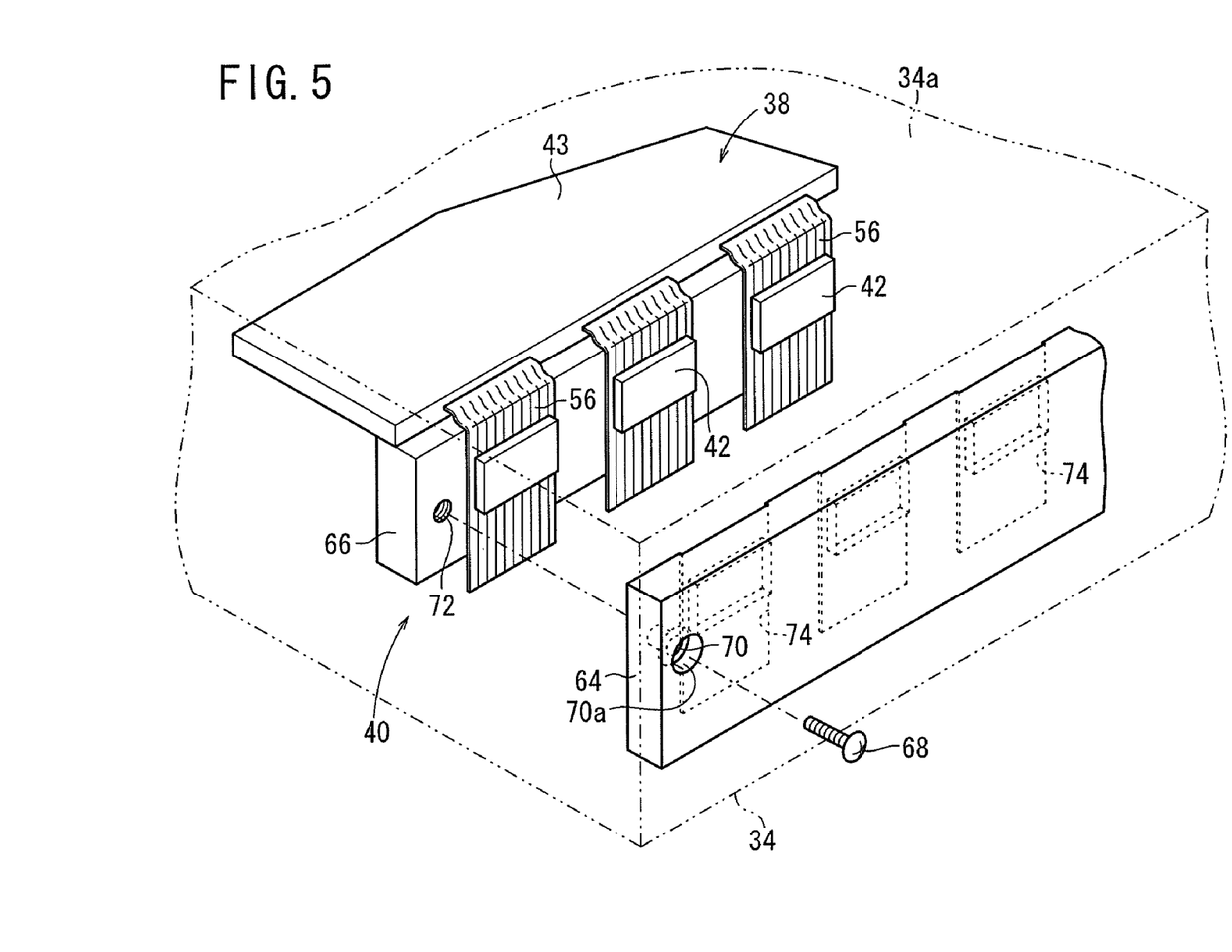
FIG. 5 is an enlarged, partially exploded schematic perspective view of part of the radiation detecting device shown in FIG. 2.

Hereinafter, the heat release member 40 will be described in detail with particular reference to FIGS. 5 and 6. FIG. 5 is an enlarged, partially exploded perspective view of part of the radiation detecting device 32, and FIG. 6 is a partially-omitted cross-sectional view of the radiation detecting device 32 taken along line VI-VI in FIG. 3.

The heat release member 40 includes a first heat release member 64 that is disposed on one side (outer side) of the reading ICs 42 and the signal lines 56, and a second heat release member 66 that is disposed on the other side (inner side) of the reading ICs 42 and the signal lines 56 so as to be in close contact with the first heat release member 64. The heat release member 40 is arranged so that the reading ICs 42 and the signal lines 56 are tightly held between the first and second heat release members 64 and 66.

The heat release member 40, i.e., the first and second heat release members 64 and 66, is made of a highly heat-conductive material such as an alloy of, for example, aluminum, copper, iron, or lead. As shown in FIGS. 3 and 5, the first and second heat release members 64 and 66 have an elongated rectangular shape that extends over the plurality of reading ICs 42 and signal lines 56 disposed along the sensor substrate 43. It should be understood that the first and second heat release members 64 and 66 may be made up of shorter pieces than that shown in FIG. 3, and two or more of such pieces may be used in combination.

Figure 6:
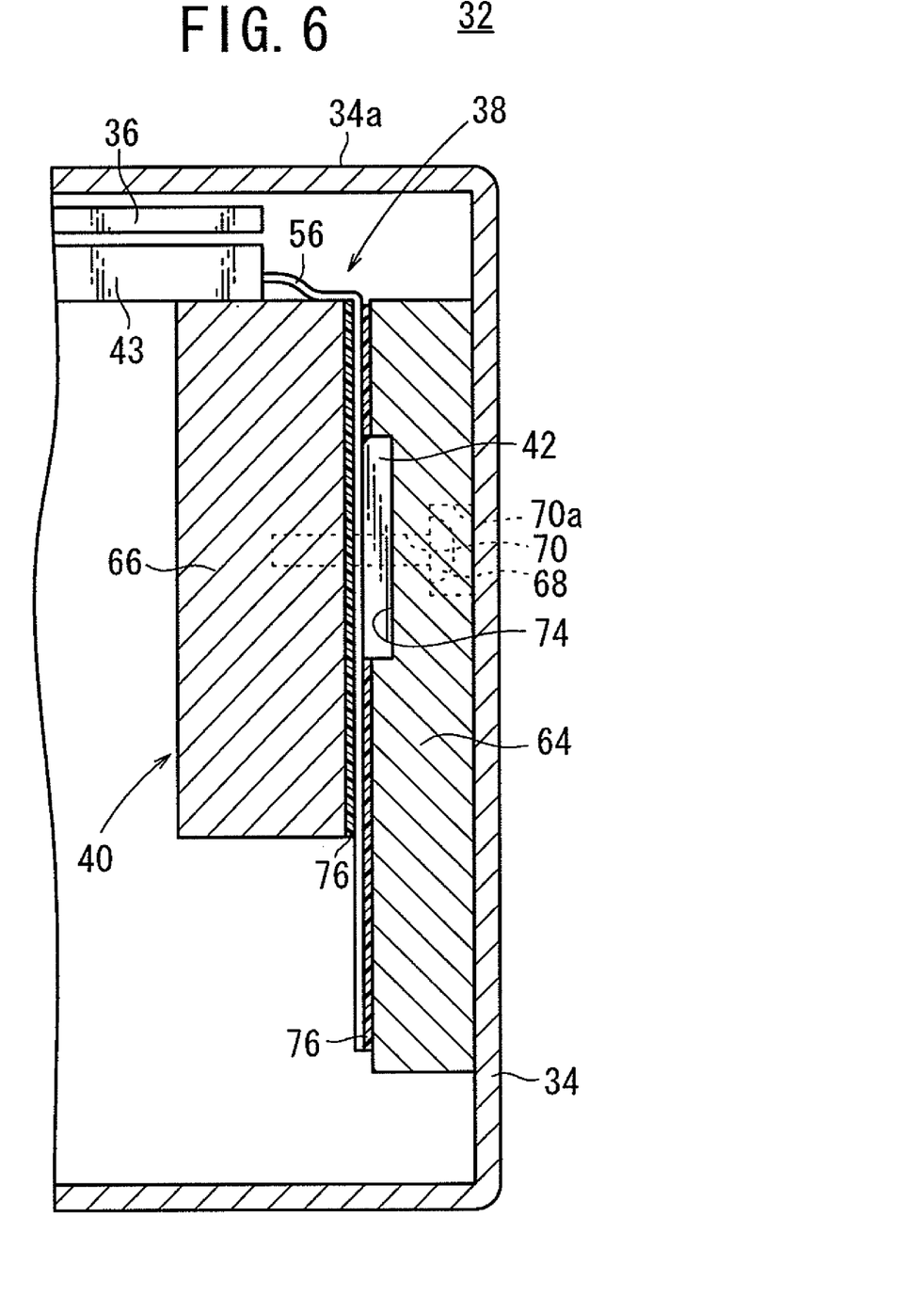
FIG. 6 is a partially-omitted cross-sectional view taken along line VI-VI in FIG. 3.

As shown in FIGS. 5 and 6, the outer surface of the first heat release member 64 (i.e., the surface of the first heat release member 64 opposite to that facing the second heat release member 66) is tightly attached to the inner surface of the casing 34, and the second heat release member 66 is fastened to the first heat release member 64. Specifically, a threaded portion of a bolt 68, for example, is passed through a through hole 70 of the first heat release member 64 and threadably coupled with a screw hole 72 of the second heat release member 66 to fasten the first and second heat release members 64 and 66 to each other in close contact. Note that the reference number 70a in FIG. 5 indicates a counterbore that is formed in the first heat release member 64 in order to keep the head portion of the bolt 68 out of view.

In order to ensure close contact between the first and second heat release members 64 and 66 with the reading ICs 42 and the signal lines 56 held therebetween, the inner surface of the first heat release member 64, i.e., the surface facing the second heat release member 66, is provided with concave portions 74 to accommodate the reading ICs 42 and the signal lines 56. The depth of each concave portion 74 is defined so that, when the first and second heat release members 64 and 66 are closely attached to each other, the bottom of the concave portion 74 and the outer surface of the second heat release member 66 (i.e., the surface facing the first heat release member 64) reliably come into close contact with the heat generating reading IC 42 and the signal lines 56 (see FIG. 6).

Sealing members 76 having high heat conductivity are introduced (filled) between the first and second heat release members 64, 66 and the reading IC 42 and signal line 56. That is, as shown in FIG. 6, the sealing member 76 is interposed at least between the first heat release member 64 and one surface of the signal line 56, and at least between the second heat release member 66 and the other surface of the signal line 56. The sealing members 76 ensure close contact of the first and second heat release members 64 and 66 with the reading ICs 42 and signal lines 56 and also enhance heat transfer from the reading ICs 42 or the signal lines 56 to the first and second heat release members 64 and 66. The sealing member 76 may be, for example, a soft, paste like gel member, a gel sheet, or the like that has high heat conductivity and, preferably, electrical insulating properties. Such a sealing member 76 may also be disposed between the first and second heat release members 64 and 66 in areas where they are closely attached to each other without the reading ICs 42 or the signal lines 56 therebetween, and also disposed on close contact surfaces between the outer surface of the first heat release member 64 and the casing 34.

Figure 7:
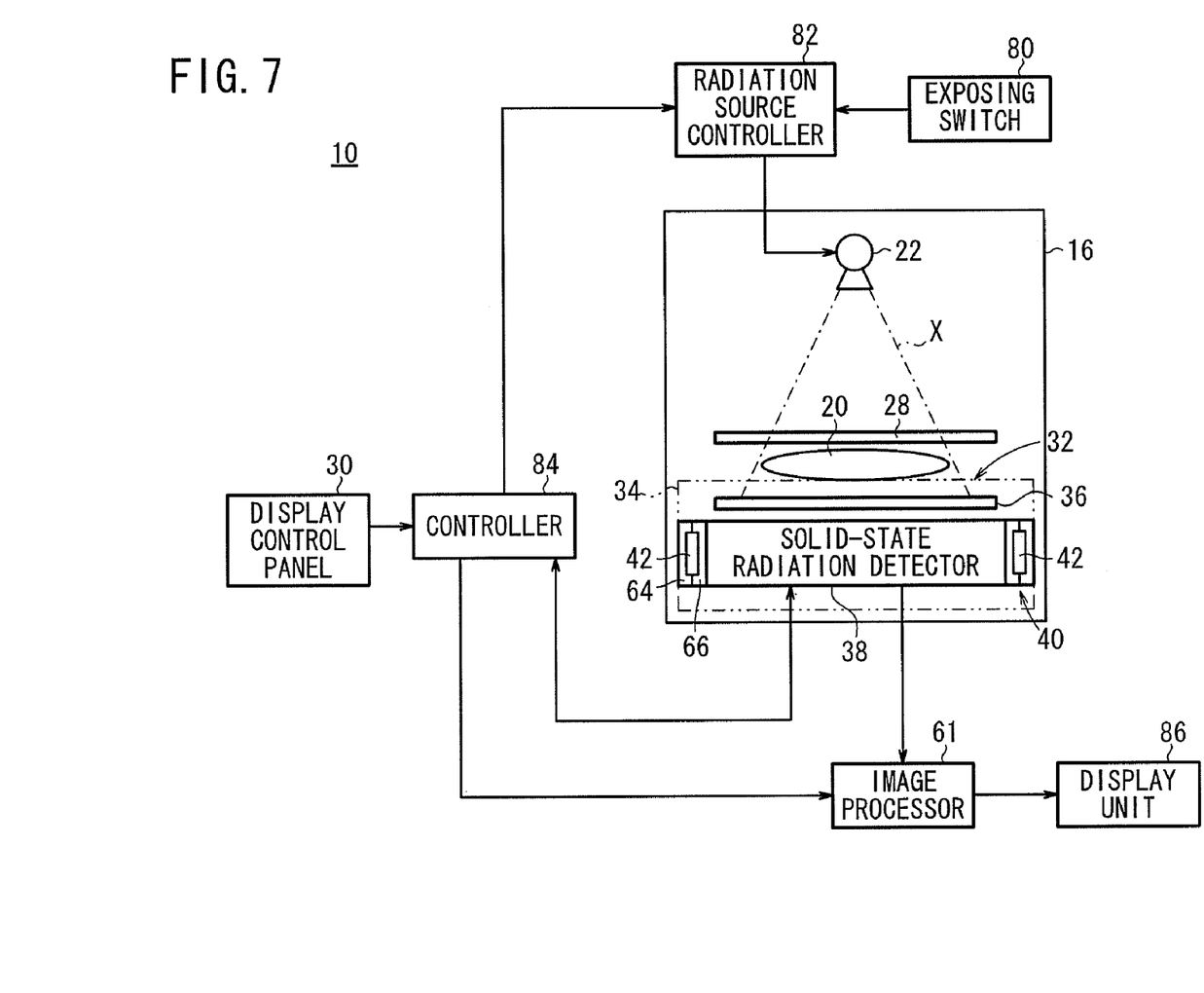
FIG. 7 is a block diagram illustrating the configuration of the mammography apparatus shown in FIG. 1.

FIG. 7 is a block diagram illustrating the configuration of the mammography apparatus 10 according to the embodiment of the present invention.

As shown in FIG. 7, the mammography apparatus 10 includes a radiation source controller 82 for controlling the radiation source 22 that is placed within the radiation source housing unit 24 and emits radiation X on the operation of an exposure switch 80, the radiation detecting device 32 that includes the solid-state radiation detector 38 for detecting radiation X that has passed through the subject 18, the heat release member 40 and the like in the casing 34, and a controller 84 (controlling unit) for controlling the radiation source controller 82 and the radiation detecting device 32. The mammography apparatus 10 further includes the image processor 61 for performing predetermined image processing on radiation image information of the subject 18 read out from the solid-state radiation detector 38, and a display unit 86 for displaying the processed radiation image information.

The operation of the mammography apparatus 10 according to the present embodiment, which is basically configured as discussed above, will now be described.

First, ID information about the subject 18, image capturing conditions, and the like are provided to the mammography apparatus 10 through the display control panel 30, a console (not shown), or the like. The ID information may include the name, age, gender, or the like of the subject 18 and can be acquired from an ID card of the subject 18. If the mammography apparatus 10 is connected to a network, the ID information may also be acquired from other apparatuses on the network. The image capturing conditions may include an image capturing site, an image capturing direction, and the like specified by the physician, and also the amount of radiation exposure corresponding to the image capturing site. These items of information may be acquired from a higher-level apparatus on the network or entered through the display control panel 30 or the console by a radiologist. The ID information, image capturing conditions, and the like may be displayed on the display control panel 30 of the mammography apparatus 10 for verification.

The radiologist then sets the mammography apparatus 10 in accordance with the specified image capturing conditions. The image capturing direction of the breast 20 may include, for example, a craniocaudal view (CC), a mediolateral view (ML), or a mediolateral oblique view (MLO), in which image is captured by exposing the breast 20 to the radiation X from the top, the side, or an oblique angle, respectively. The arm 16 is rotated about the pivot shaft 14 in accordance with the specified image capturing direction.

Next, the breast 20 of the subject 18 is positioned with respect to the mammography apparatus 10, i.e., the breast 20 is placed on the image capturing base 26, and the compression plate 28 is moved down to hold the breast 20 between the image capturing base 26 and the compression plate 28 (see FIG. 2).

After the above preparatory operations have been completed, image capturing is started.

First, the radiologist operates the exposure switch 80, so that the controller 84 controls the radiation source controller 82 according to the set image capturing condition, and the breast 20 of the subject 18 is irradiated with radiation X. The radiation X that has passed through the breast 20 is converted into an electrical signal by the photoelectric conversion layer 51 of each pixel 50 making up the sensor substrate 43 of the solid-state radiation detector 38, and the electrical signal is stored into the storage capacitor 53 (see FIG. 4) as charges. Next, the charge information stored in the storage capacitors 53, which is the radiation image information of the breast 20, is read out in accordance with the timing control signals supplied from the timing control circuit 48 to the gate line driving circuit 44 and the signal reading circuit 46.

More specifically, the gate line driving circuit 44 selects one of the gate lines 54 in accordance with the timing control signal provided from the timing control circuit 48 and supplies a driving signal to the base of each TFT 52 connected to the selected gate line 54. Meanwhile, the signal reading circuit 46 selects one of the signal lines 56 connected to the reading ICs 42 successively switched in the row direction by the multiplexer 60 in accordance with the timing control signals provided from the timing control circuit 48. The charge information, which is associated with the radiation image information and stored in the storage capacitor 53 of the pixel 50 corresponding to both of the selected gate line 54 and signal line 56, is provided to the operational amplifier via the variable resistor (not shown) to be integrated. The integrated charge information is supplied to the A/D converter 62 via the multiplexer 60 and transmitted to the image processor 61 as a digital image signal. After the image signal from each pixel 50 in the row direction has been read out, the gate line driving circuit 44 selects the next gate line 54 in the column direction and supplies the driving signal to the selected gate line 54. The signal reading circuit 46 then reads out the image signals from the TFTs 52 connected to the selected gate line 54 as described above.

By repeating the operation described above, the two-dimensional radiation image information stored in the sensor substrate 43 is read out and supplied to the image processor 61. The radiation image information supplied to the image processor 61 is processed in a predetermined manner and then displayed on the display unit 86 for diagnosis or the like.

In the mammography apparatus 10 that captures radiation images of the subject 18 in the manner described above, the electronic components of the solid-state radiation detector 38 disposed in the casing 34, e.g., the reading ICs 42 making up the signal reading circuit 46, generate heat during the operation (image capturing) of the mammography apparatus 10, causing the temperature of the solid-state radiation detector 38 to increase. As described above, the solid-state radiation detector 38 may show performance degradation at high temperatures. Specifically, the performance of the amorphous selenium, for example, may be degraded due to partial or overall crystallization, making it difficult to acquire high accuracy radiation images.

In the radiation detecting device 32 of the mammography apparatus 10 according to the present embodiment, the reading ICs 42, which are the heat generating components, and the signal lines 56 are fastened by the heat release member 40 that is capable of releasing heat generated by the reading ICs 42 to the outside of the radiation detecting device 32, thereby achieving suitable cooling of the reading ICs 42.

In the mammography apparatus 10, the first and second heat release members 64 and 66 of the heat release member 40 hold the reading ICs 42 therebetween to reliably fasten the reading ICs 42, and also the signal lines 56, to the casing 34 and thereby effectively protect reading circuits including the reading ICs 42, the signal lines 56, and the connections between the reading ICs 42 and the signal lines 56 from vibrations generated by various mechanical portions in the mammography apparatus 10. In the heat release member 40, since the first heat release member 64 is attached to the inner surface of the casing 34, the heat generated by the reading ICs 42 can be suitably transferred through the first heat release member 64 or through the second and first heat release members 66 and 64 to the casing 34, allowing the casing 34 and the image capturing base 26 outside the casing 34 to be utilized as radiators like a radiation fin. The casing 34, in particular, may serve as a suitable radiator since it typically has a large surface area.

It should be noted that in addition to being used to fasten the reading ICs 42, the heat release member 40 may also be used to fasten the driving ICs 41 to the casing 34 (see the broken lines in FIG. 3). Fastening the driving ICs 41 to the casing 34 with the heat release member 40 increases the heat release efficiency of the solid-state radiation detector 38 and also protects the driving ICs 41 and the gate lines 54 from the vibrations or the like of the mammography apparatus 10. It should be understood that the heat release member 40 may also be provided so as to fasten only the driving ICs 41 to the casing 34.

As can be seen in FIGS. 3 and 6, the heat release member 40 is arranged so as to shield the signal reading circuit 46 (reading ICs 42) and the gate line driving circuit 44 (driving ICs 41) from the radiation X emitted from the radiation source 22. Typical solid-state radiation detectors require a shield plate made of lead that is arranged around the irradiated surface of the sensor substrate 43 in order to protect the reading ICs 42 and the like from radiation X. The present embodiment, however, does not need such a lead shield plate and can effectively prevent the reading ICs 42 and driving ICs 41 from being damaged by radiation X with a simple configuration. Preferably, the first and second heat release members 64 and 66 of the heat release member 40 are made of a material that has desirable radiation shielding ability as well as high heat conductivity.

Figure 8:
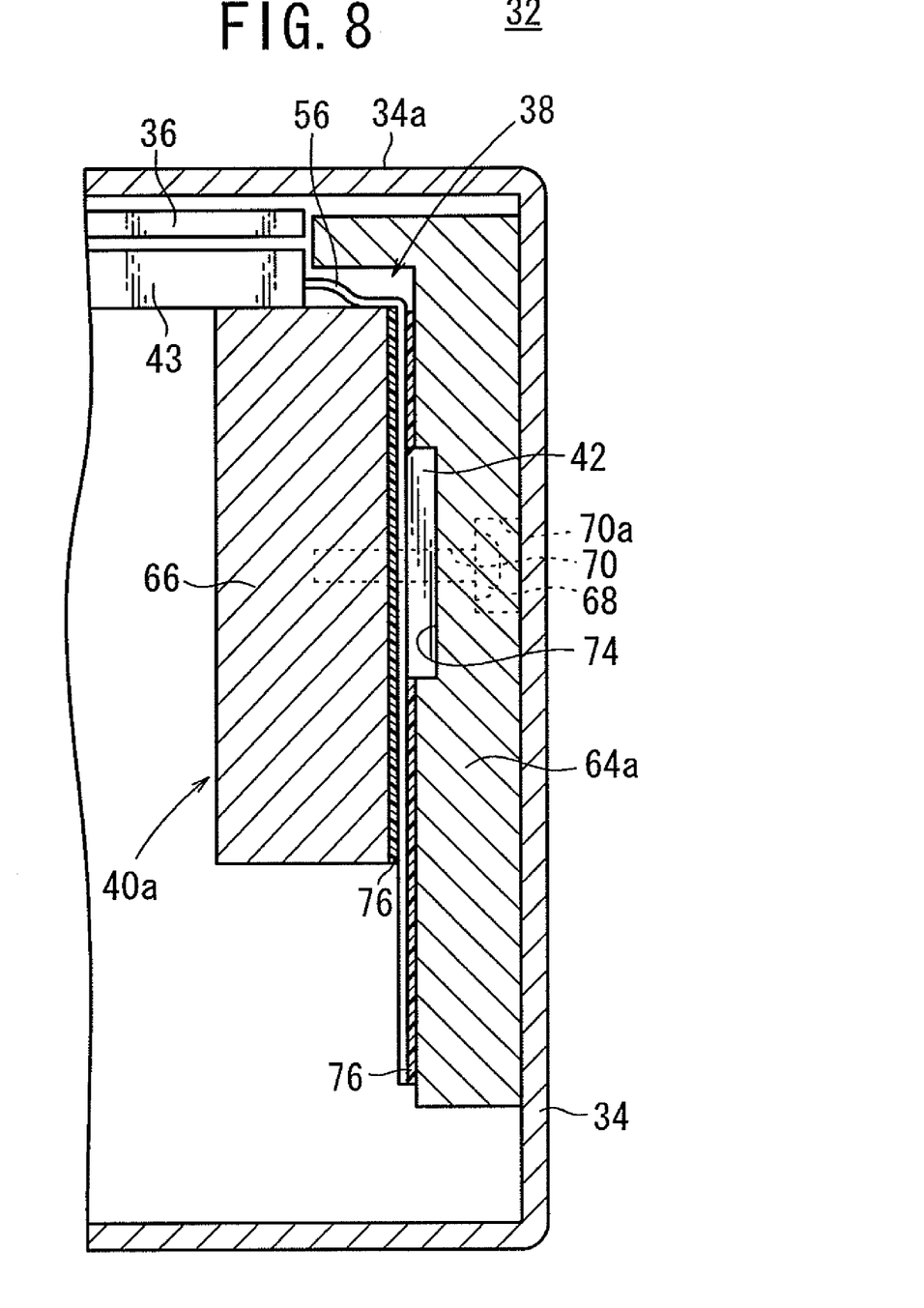
FIG. 8 is a partially-omitted cross-sectional view of a variation of a heat release member shown in FIG. 6.

As shown in FIG. 8, the heat release member 40 may be replaced with a heat release member 40a that includes a first heat release member 64a in place of the first heat release member 64. The first heat release member 64a has the same configuration as the first heat release member 64 except that the upper end (the end near to the irradiated surface 34a) is extended upwardly and bent so as to cover the upper part of the signal lines 56 (facing the irradiated surface 34a) that are exposed to the inside of the casing 34 beside the sensor substrate 43. The heat release member 40a configured in this way can effectively prevent radiation X from, for example, passing through the gel-like sealing member 76 made of an organic substance and irradiating the reading ICs 42 and driving ICs 41. Note that the upper end of the first heat release member 64a that covers the upper part of the signal lines 56 may also be formed as a separate piece.

Generally, radiation X is applied so that its center is positioned at or near the center of the sensor substrate 43. The reading ICs 42 and the driving ICs 41 located around the sensor substrate 43 are irradiated with radiation X from an oblique direction, resulting in only a small amount of radiation passing through the reading ICs 42 and driving ICs 41. Therefore, although the first heat release member 64 shown in FIG. 3 can suitably shield radiation X, the first heat release member 64a shown in FIG. 8 protects the reading ICs 42 and the driving ICs 41 from radiation X much more reliably.

In the mammography apparatus 10, the first and second heat release members 64 (64a) and 66 are grounded via the casing 34 since the first heat release member 64 (64a) is fastened to the casing 34. Thus, the heat release member 40 (40a) is kept at a constant potential and effectively shields electromagnetic noise. A ground wire may also be connected to the heat release member 40 (40a) and/or the casing 34. In the present embodiment, the heat release member 40 (40a) is made of hard metal, and the first and second heat release members 64 (64a) and 66 are reliably and firmly attached to each other by means of the bolts 68, for example. Further, the outer side of the first heat release member 64 (64a) is provided with the counterbore 70a that receives the head portion of the bolt 68 to allow the outer side of the first heat release member 64 (64a) to be fastened to the casing 34 tightly, reliably, and firmly. This configuration ensures suitable heat transfer from the heat release member 40 (40a) to the casing and more reliable shielding of electromagnetic noise.

As described above, the mammography apparatus 10 according to the present embodiment is provided with the heat release member 40 (40a) that serves as a fastening member for fastening the reading ICs 42 and signal lines 56 (and/or the driving ICs 41 and gate lines 54) and also as a heat release unit for releasing heat from the reading ICs 42 (and/or the driving ICs 41). The heat release member 40 (40a) eliminates the need for additional fastening members for fastening the reading ICs 42, signal lines 56, driving ICs 41, and gate lines 54 and the need for additional radiation fins for releasing heat from the reading ICs 42 and driving ICs 41, in the casing 34. Thus, the mammography apparatus 10 can be made in a more simple and compact configuration. In the mammography apparatus 10 of the present embodiment, in which it is difficult to increase the size of the image capturing base 26 that contains the radiation detecting device 32, the use of the heat release member 40 (40a) is particularly advantageous for downsizing of the apparatus and enhancement of electronic components' heat release. Thus, the present embodiment can prevent functional deterioration of the solid-state radiation detector 38 and allows high-quality images to be produced, while making it possible to provide more simple and compact apparatuses. The use of the heat release member 40 (40a) eliminates the need for providing the radiation detecting device 32 with a lead shielding plate or the like in order to protect the reading ICs 42 and the like from radiation X, and thus the mammography apparatus can be more simply configured. The use of the heat release member 40 (40a) also allows acquisition of high-quality radiation images, since the heat release member 40 (40a) can shield the electromagnetic noise generated by the solid-state radiation detector 38.

The present invention is not limited to the embodiment described above and can be modified without departing from the scope of the invention.

In the embodiment described above, the heat release member 40 (40a) is made up of multiple pieces, (i.e., the first and second heat release members 64 and 66,) and the reading ICs 42 and signal lines 56 (driving ICs 41 and gate lines 54) are held between the first and second heat release members 64 and 66. The heat release member 40 (40a), however, may be configured from a single piece. The single piece heat release member may have a U-shape cross-section, for example, and one of its side surfaces may be attached to the casing 34. The reading ICs 42, the signal lines 56, and the like may be received within a recessed portion formed at the center of the U-shape heat release member.

Alternatively, the heat release member may be a single piece fastened simply to the casing 34, the reading ICs 42, the signal lines 56, and the like may be attached thereto.

In the embodiments described above, a TFT substrate is used as an active matrix substrate. The TFT substrate may be configured arbitrarily, e.g., by a TFT substrate having TFTs of amorphous silicon (a-Si) on a glass substrate, a TFT substrate having organic TFTs on a resin substrate, or the like. Further, another active matrix substrate may be used, such as an active matrix substrate having CCD (Charge Coupled Device) or CMOS (Complementary Metal Oxide Semiconductor) sensors on a silicon substrate.

The solid-state radiation detector 38 described above converts the incident radiation X directly into an electrical signal corresponding to the amount of the radiation X by means of the photoelectric conversion layer 51 (i.e., direct conversion type). Instead, the solid-state radiation detector 38 may, however, be configured to convert the incident radiation X into visible light with a scintillator and then the visible light into an electrical signal using solid-state detecting elements such as a-Si (i.e., indirect conversion type, see Japanese Patent No. 3494683).

The radiation image information may also be acquired with light readout type radiation detectors. In light readout type radiation detectors, a two-dimensional array of solid-state detecting elements receives radiation and stores a latent image corresponding to the amount of radiation. Readout of the latent image is carried out by applying reading light onto the radiation detector and utilizing the value of the electrical current generated by the radiation detector as radiation image information. The latent image, or the radiation image information of the radiation detector can be erased by irradiating the radiation detector with erasing light, so that the radiation detector can be reused (see Japanese Laid-Open Patent Publication No. 2000-105297).

It should be noted that the application of the radiation image capturing apparatus according to the present invention is not limited to the exemplary mammography apparatus of the embodiment described above, but can also be applied to radiation image capturing apparatuses for capturing images of other parts of the subject, such as the chest.

What is claimed is:

1. A radiation image capturing apparatus, comprising:
a radiation image information detector for detecting radiation image information of a subject obtained by irradiating the subject with radiation emitted from a radiation source;
a casing containing the radiation image information detector; and
a heat release unit, wherein
the radiation image information detector includes a sensor substrate, a driving circuit for driving a gate line connected to a pixel of the sensor substrate, and a reading circuit for reading out charge information from the pixel through a signal line,
the heat release unit has a first heat release member and a second heat release member, the sensor substrate having a first surface that contacts the second heat release member, and the second heat release member is spaced from one surface of the casing, wherein said one surface is opposite said first surface, and
the first heat release member is extended on a side irradiated with the radiation so as to cover the signal line connected to the sensor substrate.

2. The radiation image capturing apparatus according to claim 1, wherein the reading circuit comprises a reading integrated circuit, and the first heat release member is arranged on one side of the reading integrated circuit and the second heat release member is arranged on another side of the reading integrated circuit.

3. The radiation image capturing apparatus according to claim 1, wherein a grid which removes the radiation that has been scattered by the subject, the radiation image information detector, and the first and second heat release members which release heat from the reading circuit of the radiation image information detector are arranged inside the casing.

4. The radiation image capturing apparatus according to claim 1, wherein the driving circuit is formed of a driving integrated circuit for driving the gate line connected to the pixel of the sensor substrate, and the reading circuit is formed of a reading integrated circuit for reading out the charge information from a pixel through a signal line, and the heat release unit is disposed on the reading integrated circuit.

5. The radiation image capturing apparatus according to claim 4, wherein a third heat release member is disposed on each of the driving integrated circuit and the gate line.

6. The radiation image capturing apparatus according to claim 1, wherein the first heat release member has an elongated shape that extends over a reading integrated circuit of the reading circuit and the signal line that are disposed along the sensor substrate.

7. The radiation image capturing apparatus according to claim 1, wherein one surface of the first heat release member has a concave portion to accommodate a reading integrated circuit of the reading circuit and the signal line connected to the reading integrated circuit.

8. The radiation image capturing apparatus according to claim 7, wherein a depth of the concave portion is defined so that, in a state that the first and second heat release members are fastened, a bottom of the concave portion and an outer surface of the second heat release member come into contact with the reading integrated circuit and the signal line.

9. The radiation image capturing apparatus according to claim 1, wherein an attaching member is introduced between the first and second heat release members and a reading integrated circuit of the reading circuit and the signal line.

10. The radiation image capturing apparatus according to claim 9, wherein the attaching member has electrical insulating properties.

11. The radiation image capturing apparatus according to claim 1, wherein the first heat release member is positioned so as to shield the reading circuit from the radiation.

12. The radiation image capturing apparatus according to claim 1, wherein the first heat release member includes a space to put a reading integrated circuit of the radiation image information detector and the signal line connected to the reading integrated circuit in the space.

13. A radiation image capturing apparatus, comprising:
a radiation image information detector for detecting radiation image information of a subject obtained by irradiating the subject with radiation emitted from a radiation source;
a casing containing the radiation image information detector; and
a heat release unit, wherein
the radiation image information detector includes a sensor substrate, a driving circuit for driving a gate line connected to a pixel of the sensor substrate, and a reading circuit for reading out charge information from the pixel through a signal line, and
the heat release unit has a first heat release member and a second heat release member, the sensor substrate having a first surface that contacts the second heat release member, the second heat release member is spaced from one surface of the casing, wherein said one surface is opposite said first surface, the reading circuit is interposed between the first heat release member and the second heat release member, the signal line connected to the reading circuit is arranged between a bent portion of the first heat release member and the second heat release member, and the first heat release member contacts an inner surface of the casing so as to release to the exterior via the casing heat that is generated by the reading circuit in operation.

14. The radiation image capturing apparatus according to claim 13, wherein the first heat release member and the second heat release member hold a reading integrated circuit of the reading circuit therebetween and cover the signal line connected to the sensor substrate.

15. The radiation image capturing apparatus according to claim 13, wherein a part of the first heat release member is bent to extend toward the sensor substrate.

16. The radiation image capturing apparatus according to claim 13, wherein the reading circuit and a part of the signal line connected to the reading circuit are interposed between the first heat release member and the second heat release member, and the first heat release member and the second heat release member are fastened to each other by a fastening unit.

17. The radiation image capturing apparatus according to claim 16, wherein the fastening unit comprises a bolt by which the first heat release member and the second heat release member are fastened.

18. The radiation image capturing apparatus according to claim 13, wherein the reading circuit comprises a reading integrated circuit, and the first heat release member is arranged on one side of the reading integrated circuit and the second heat release member is arranged on another side of the reading integrated circuit.

19. The radiation image capturing apparatus according to claim 13, wherein a grid which removes the radiation that has been scattered by the subject, the radiation image information detector, and the first and second heat release members which release heat from a reading integrated circuit of the reading circuit are arranged inside the casing.

20. The radiation image capturing apparatus according to claim 13, wherein the driving circuit is formed of a driving integrated circuit for driving the gate line connected to the pixel of the sensor substrate, and the reading circuit is formed of a reading integrated circuit for reading out the charge information from a pixel through a signal line, and the heat release unit is disposed on the reading integrated circuit.

21. The radiation image capturing apparatus according to claim 20, wherein a third heat release member is disposed on each of the driving integrated circuit and the gate line.

22. The radiation image capturing apparatus according to claim 13, wherein the first heat release member has an elongated shape that extends over a reading integrated circuit of the reading circuit and the signal line that are disposed along the sensor substrate.

23. The radiation image capturing apparatus according to claim 13, wherein one surface of the first heat release member has a concave portion to accommodate a reading integrated circuit of the reading circuit and the signal line connected to the reading integrated circuit.

24. The radiation image capturing apparatus according to claim 23, wherein a depth of the concave portion is defined so that, in a state that the first and second heat release members are fastened, a bottom of the concave portion and an outer surface of the second heat release member come into contact with the reading integrated circuit and the signal line.

25. The radiation image capturing apparatus according to claim 13, wherein an attaching member is introduced between the first and second heat release members and the reading integrated circuit and the signal line.

26. The radiation image capturing apparatus according to claim 25, wherein the attaching member has electrical insulating properties.

27. The radiation image capturing apparatus according to claim 13, wherein the second heat release member is positioned so as to shield the reading circuit from the radiation.

28. The radiation image capturing apparatus according to claim 13, wherein the first heat release member includes a space to put a reading integrated circuit of the radiation image information detector and the signal line connected to the reading integrated circuit in the space.

29. A radiation image capturing apparatus, comprising:
a radiation image information detector for detecting radiation image information of a subject obtained by irradiating the subject with radiation emitted from a radiation source;
a casing containing the radiation image information detector; and
a heat release unit, wherein
the radiation image information detector includes a sensor substrate, a driving circuit for driving a gate line connected to a pixel of the sensor substrate, and a reading circuit for reading out charge information from the pixel through a signal line,
the heat release unit has a first heat release member and a second heat release member, the second heat release member contacting the sensor substrate of the radiation image information detector, and the first heat release member is extended on a side irradiated with the radiation so as to cover the signal line connected to the sensor substrate, and
the reading circuit is interposed between the first heat release member and the second heat release member, the first heat release member and the second heat release member are fastened to each other by a fastening unit, and the fastening unit does not extend through the casing.

30. The radiation image capturing apparatus according to claim 29, wherein the reading circuit comprises a reading integrated circuit, and the first heat release member is arranged on one side of the reading integrated circuit and the second heat release member is arranged on another side of the reading integrated circuit.

31. The radiation image capturing apparatus according to claim 29, wherein a grid which removes the radiation that has been scattered by the subject, the radiation image information detector, and the first and second heat release members which release heat from the reading circuit of the radiation image information detector are arranged inside the casing.

32. The radiation image capturing apparatus according to claim 29, wherein the driving circuit is formed of a driving integrated circuit for driving the gate line connected to the pixel of the sensor substrate, and the reading circuit is formed of a reading integrated circuit for reading out the charge information from a pixel through a signal line, and the heat release unit is disposed on the reading integrated circuit.

33. The radiation image capturing apparatus according to claim 32, wherein a third heat release member is disposed on each of the driving integrated circuit and the gate line.

34. The radiation image capturing apparatus according to claim 29, wherein the first heat release member has an elongated shape that extends over a reading integrated circuit of the reading circuit and the signal line that are disposed along the sensor substrate.

35. The radiation image capturing apparatus according to claim 29, wherein one surface of the first heat release member has a concave portion to accommodate a reading integrated circuit of the reading circuit and the signal line connected to the reading integrated circuit.

36. The radiation image capturing apparatus according to claim 35, wherein a depth of the concave portion is defined so that, in a state that the first and second heat release members are fastened, a bottom of the concave portion and an outer surface of the second heat release member come into contact with the reading integrated circuit and the signal line.

37. The radiation image capturing apparatus according to claim 29, wherein an attaching member is introduced between the first and second heat release members and a reading integrated circuit of the reading circuit and the signal line.

38. The radiation image capturing apparatus according to claim 37, wherein the attaching member has electrical insulating properties.

39. The radiation image capturing apparatus according to claim 29, wherein the heat release members are positioned so as to shield the reading circuit from the radiation.

40. A radiation image capturing apparatus, comprising:
a radiation image information detector for detecting radiation image information of a subject obtained by irradiating the subject with radiation emitted from a radiation source;
a casing containing the radiation image information detector; and
a heat release unit, wherein
the radiation image information detector includes a sensor substrate, a driving circuit for driving a gate line connected to a pixel of the sensor substrate, and a reading circuit for reading out charge information from the pixel through a signal line, and
the heat release unit has a first heat release member and a second heat release member, the second heat release member contacting the sensor substrate of the radiation image information detector, the reading circuit is interposed between the first heat release member and the second heat release member, the signal line connected to the reading circuit is arranged between a bent portion of the first heat release member and the second heat release member, and the first heat release member contacts an inner surface of the casing so as to release to the exterior via the casing heat that is generated by the reading circuit in operation, and the reading circuit is interposed between the first heat release member and the second heat release member, the first heat release member and the second heat release member are fastened to each other by a fastening unit, and the fastening unit does not extend through the casing.

41. The radiation image capturing apparatus according to claim 40, wherein the first heat release member and the second heat release member hold a reading integrated circuit of the reading circuit therebetween and cover the signal line connected to the sensor substrate.

42. The radiation image capturing apparatus according to claim 40, wherein a part of the first heat release member is bent to extend toward the sensor substrate.

43. The radiation image capturing apparatus according to claim 40, wherein the fastening unit comprises a bolt by which the second heat release member and the second heat release member are fastened.

44. The radiation image capturing apparatus according to claim 40, wherein the reading circuit comprises a reading integrated circuit, and the first heat release member is arranged on one side of the reading integrated circuit and the second heat release member is arranged on another side of the reading integrated circuit.

45. The radiation image capturing apparatus according to claim 40, wherein a grid which removes the radiation that has been scattered by the subject, the radiation image information detector, and the first and second heat release members which release heat from a reading integrated circuit of the reading circuit are arranged inside the casing.

46. The radiation image capturing apparatus according to claim 40, wherein the driving circuit is formed of a driving integrated circuit for driving the gate line connected to the pixel of the sensor substrate, and the reading circuit is formed of a reading integrated circuit for reading out the charge information from a pixel through a signal line, and the heat release unit is disposed on the reading integrated circuit.

47. The radiation image capturing apparatus according to claim 46, wherein a third heat release member is disposed on each of the driving integrated circuit and the gate line.

48. The radiation image capturing apparatus according to claim 40, wherein the first heat release member has an elongated shape that extends over a reading integrated circuit of the reading circuit and the signal line that are disposed along the sensor substrate.

49. The radiation image capturing apparatus according to claim 40, wherein one surface of the first heat release member has a concave portion to accommodate a reading integrated circuit of the reading circuit and the signal line connected to the reading integrated circuit.

50. The radiation image capturing apparatus according to claim 49, wherein a depth of the concave portion is defined so that, in a state that the first and second heat release members are fastened, a bottom of the concave portion and an outer surface of the second heat release member come into contact with the reading integrated circuit and the signal line.

51. The radiation image capturing apparatus according to claim 40, wherein an attaching member is introduced between the first and second heat release members and the reading integrated circuit and the signal line.

52. The radiation image capturing apparatus according to claim 51, wherein the attaching member has electrical insulating properties.

53. The radiation image capturing apparatus according to claim 40, wherein the second heat release member is positioned so as to shield the reading circuit from the radiation.

* * * * *